United States Patent
Elliott et al.

(10) Patent No.: US 7,540,868 B2
(45) Date of Patent: Jun. 2, 2009

(54) MEDICAL SUCTION DEVICE

(75) Inventors: Bradley D. Elliott, Superior, CO (US); Clifford M. Liu, Randolf, MA (US); Jeffrey C. Smith, Poland, IN (US); Juli L. Curtis, Bloomington, IN (US); Thomas B. Remm, Cincinnati, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1251 days.

(21) Appl. No.: 10/287,060

(22) Filed: Nov. 4, 2002

(65) Prior Publication Data
US 2003/0078566 A1    Apr. 24, 2003

Related U.S. Application Data

(63) Continuation of application No. 09/844,490, filed on Apr. 27, 2001, now Pat. No. 6,517,531.

(51) Int. Cl.
*A61N 5/06* (2006.01)
*A61B 17/20* (2006.01)

(52) U.S. Cl. .......................................... 606/2.5; 604/22

(58) Field of Classification Search .............. 606/2.5, 606/27, 15, 180, 167, 127, 128, 210, 1, 107, 606/5; 604/119, 266, 260, 902, 313, 315, 604/169, 30, 246, 247, 411, 412, 413, 414, 604/415, 478, 22, 118, 129; 600/339, 158, 600/159, 114
See application file for complete search history.

(56) References Cited

U.S. PATENT DOCUMENTS

| 3,823,717 | A | 7/1974 | Pohlman et al. |
| 3,941,121 | A | 3/1976 | Olinger et al. |
| 4,146,019 | A | 3/1979 | Bass et al. |
| 4,207,874 | A | 6/1980 | Choy |
| 4,418,688 | A | 12/1983 | Loeb |
| 4,609,368 | A | 9/1986 | Dotson, Jr. |

(Continued)

FOREIGN PATENT DOCUMENTS

DE    3711086    10/1998

(Continued)

OTHER PUBLICATIONS

International Search Report for International Patent Application No. PCT/US02/13248, dated Aug. 6, 2002, 7 pages.

*Primary Examiner*—Daniel L Robinson
(74) *Attorney, Agent, or Firm*—Finnegan, Henderson, Farabow, Garrett and Dunner LLP

(57) ABSTRACT

A medical device for fragmenting objects and aspirating remaining debris enables a physician or other medical personnel quickly and easily remove objects, such as kidney stones, from a patient. The medical device can include a dual-lumen elongated member and a handle coupled to the elongated member. A first one of the lumens provides a suction passageway, and a second one of the lumens receives a laser fiber for delivering laser energy to an object, such as a kidney stone, within the patient. The handle can include a positioning mechanism to enable the physician by manual manipulation to move and hold in place the laser fiber longitudinally within the second lumen.

47 Claims, 8 Drawing Sheets

U.S. PATENT DOCUMENTS

| | | | |
|---|---|---|---|
| 4,660,573 A | 4/1987 | Brumbach | |
| 4,686,979 A | 8/1987 | Gruen et al. | |
| 4,692,139 A | 9/1987 | Stiles | |
| 4,867,141 A | 9/1989 | Nakada et al. | |
| 4,932,954 A | 6/1990 | Wondrazek et al. | |
| 5,059,200 A | 10/1991 | Tulip | |
| 5,127,393 A | 7/1992 | McFarlin et al. | |
| 5,151,098 A | 9/1992 | Loertscher | |
| 5,215,527 A * | 6/1993 | Beck et al. | 604/164 |
| 5,226,885 A * | 7/1993 | Takahashi | 604/118 |
| 5,257,991 A | 11/1993 | Fletcher et al. | |
| 5,271,735 A | 12/1993 | Greenfield et al. | |
| 5,295,956 A * | 3/1994 | Bales et al. | 604/30 |
| 5,318,024 A | 6/1994 | Kittrell et al. | 600/478 |
| 5,324,282 A | 6/1994 | Dodick | |
| 5,333,609 A | 8/1994 | Bedingham et al. | |
| 5,419,769 A * | 5/1995 | Devlin et al. | 604/119 |
| 5,429,596 A | 7/1995 | Arias et al. | |
| 5,437,659 A | 8/1995 | Leckrone | |
| 5,449,357 A | 9/1995 | Zinnanti | |
| 5,476,450 A | 12/1995 | Ruggio | |
| 5,484,402 A | 1/1996 | Saravia et al. | |
| 5,588,952 A | 12/1996 | Dandolu | |
| 5,599,299 A | 2/1997 | Weaver et al. | |
| 5,607,389 A * | 3/1997 | Edwards et al. | 604/22 |
| 5,607,420 A | 3/1997 | Schuman | |
| 5,642,370 A | 6/1997 | Mitchell et al. | |
| 5,643,250 A | 7/1997 | O'Donnell, Jr. | |
| 5,644,585 A | 7/1997 | Mitchell et al. | |
| 5,667,475 A | 9/1997 | Laser et al. | |
| 5,709,698 A | 1/1998 | Adams et al. | |
| 5,718,709 A | 2/1998 | Considine et al. | |
| 5,722,980 A | 3/1998 | Schulz et al. | |
| 5,741,244 A | 4/1998 | Klaas | |
| 5,830,224 A | 11/1998 | Cohn et al. | |
| 5,855,577 A * | 1/1999 | Murphy-Chutorian et al. | 606/7 |
| 5,861,002 A * | 1/1999 | Desai | 606/210 |
| 5,957,914 A | 9/1999 | Cook et al. | |
| 6,022,309 A | 2/2000 | Celliers et al. | |
| 6,066,131 A * | 5/2000 | Mueller et al. | 606/15 |
| 6,120,498 A * | 9/2000 | Jani et al. | 606/16 |
| 6,152,918 A * | 11/2000 | Padilla et al. | 606/15 |
| 6,238,391 B1 * | 5/2001 | Olsen et al. | 606/41 |
| 6,375,651 B2 | 4/2002 | Grasso et al. | |
| 6,440,061 B1 * | 8/2002 | Wenner et al. | 600/114 |
| 6,632,193 B1 * | 10/2003 | Davison et al. | 604/22 |
| D517,531 S * | 3/2006 | Lai | 606/2.5 |
| 2001/0027316 A1 | 10/2001 | Gregory | |
| 2002/0065512 A1 | 5/2002 | Fjield et al. | |

FOREIGN PATENT DOCUMENTS

| | | |
|---|---|---|
| EP | 0 888 750 A1 | 1/1999 |
| WO | 93/14700 | 8/1993 |
| WO | 95/24867 | 9/1995 |
| WO | 96/32895 | 10/1996 |

* cited by examiner

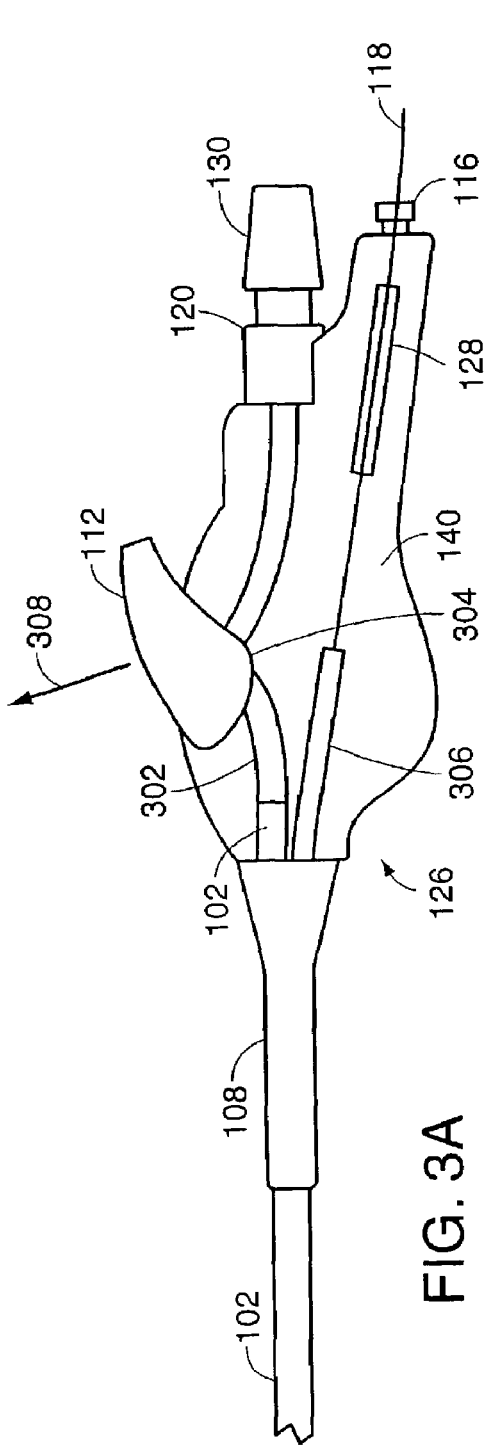
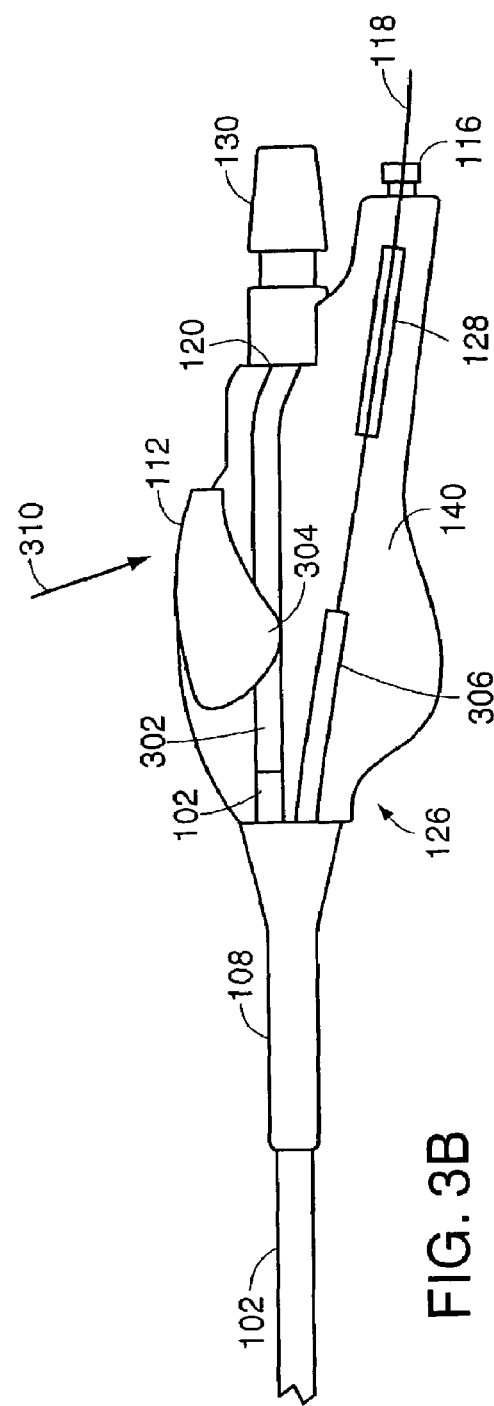

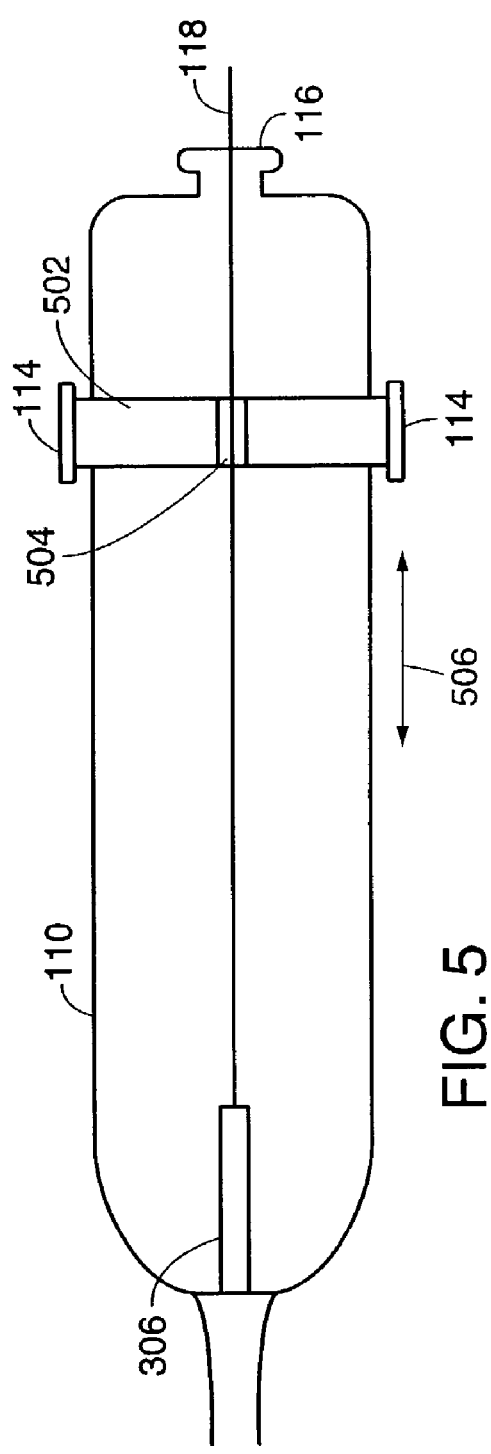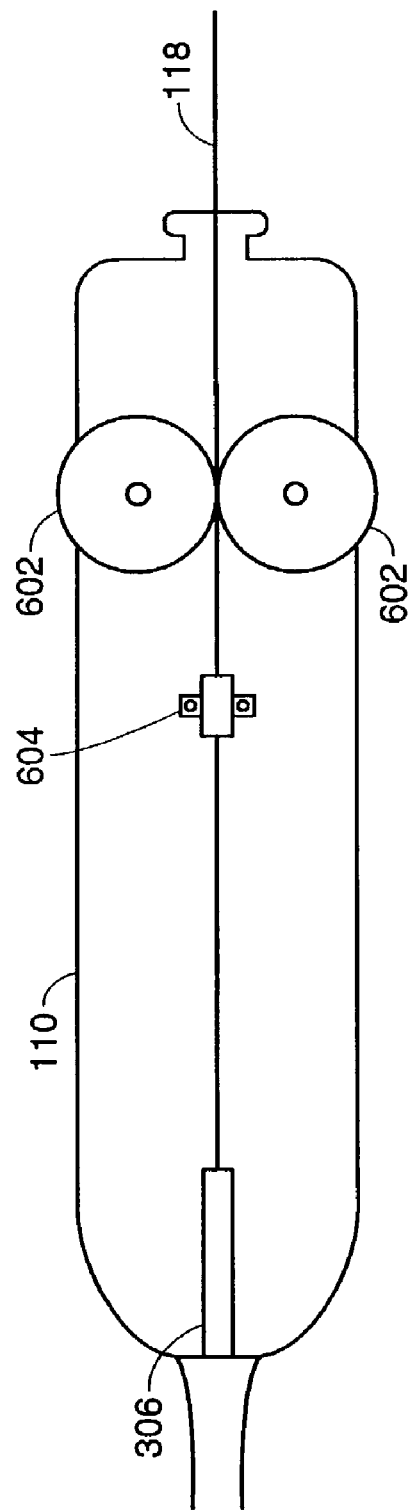

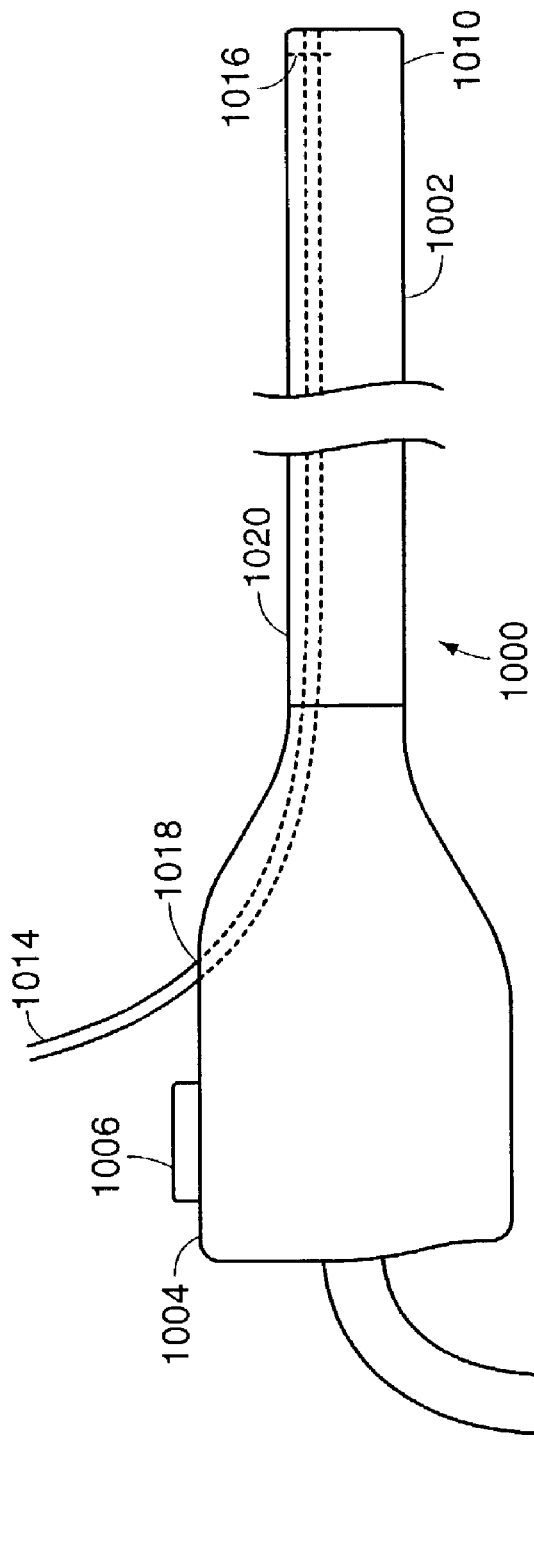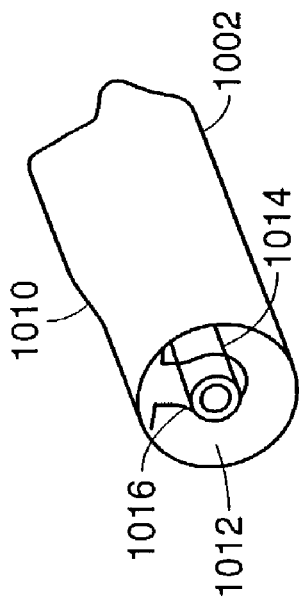
FIG. 10A
FIG. 10B

MEDICAL SUCTION DEVICE

TECHNICAL FIELD

The invention relates generally to medical suction devices and more particularly to suction devices that are used together with a mechanism for destroying or fragmenting objects within the body of a patient.

BACKGROUND INFORMATION

Suction devices can be used in the body to remove objects and fragments of objects, such as stones, other calculi, and/or tissue, as well as fragments thereof. A laser fiber can be used to deliver laser energy to such objects and/or fragments to fragment the objects and/or fragments.

SUMMARY OF THE INVENTION

The invention relates generally to medical suction devices and more particularly to suction devices that are used together with object-destroying or object-fragmenting mechanisms such as a laser fiber. Such devices and mechanisms typically are introduced into the body of a patient through a channel of a scope, such as a rigid, semi-rigid, or flexible nephroscope, to fragment and aspirate objects and fragments of objects, such as kidney stones, other calculi, and/or tissue, as well as fragments thereof.

In one aspect, the invention involves a medical device. The medical device includes a dual-lumen elongated member. The dual-lumen elongated member includes a proximal end and a distal end. A first one of the lumens provides a suction passageway and a second one of the lumens receives a laser fiber which delivers laser energy through the second lumen and beyond the distal end of the elongated member. The medical device further includes a handle coupled to the proximal end of the elongated member. The handle includes a housing which defines a cavity, a first proximal opening, and a second proximal opening. The first proximal opening receives the laser fiber and allows the laser fiber to pass through the cavity and the second lumen and out of the distal end of the elongated member. The handle further includes a suction tube disposed within the cavity and in fluid communication with the first lumen and the second proximal opening. The suction tube is flexible and selectively collapsible to control suction through the first lumen. The handle further includes a positioning mechanism. At least a portion of the positioning mechanism is disposed within the cavity and another portion is external to the housing. The positioning mechanism contacts the laser fiber and allows the laser fiber to be moved longitudinally within the second lumen by manual manipulation of the external portion of the positioning mechanism by an operator of the medical device.

In one embodiment, the handle further includes a suction control mechanism for controlling a suction path within the suction tube. The suction control mechanism crimps the suction tube and seals the suction path when the suction control mechanism is in a first position and uncrimps the suction tube and opens the suction path when the suction control mechanism is in a second position. The suction control mechanism includes a button or a lever.

In another embodiment, the dual-lumen elongated member includes a transparent material or a translucent material.

In one embodiment, the dual-lumen elongated member includes a rigid material, and in another embodiment, the dual-lumen elongated member includes a flexible material.

In some embodiments, the portion of the positioning mechanism external to the housing includes a thumb wheel, a slide bar, or a plunger.

In another embodiment, the medical device further includes a drainage tube that is external to the housing. The drainage tube includes a proximal end and a distal end. The distal end of the drainage tube is in fluid communication with the second proximal opening and the proximal end of the drainage tube is in fluid communication with a suction pump.

In still another embodiment, the distal end of the dual-lumen elongated member includes a tapered end. An outside diameter the first one of the lumens at the tapered end is smaller than an outside diameter of the first one of the lumens at the proximal end.

In yet another embodiment, the handle further includes a fiber clip for holding the laser fiber extending out of the first proximal opening.

In another aspect, the invention involves a medical device. The medical device includes a dual-lumen elongated member. The dual-lumen elongated member includes a proximal end and a distal end. A first one of the lumens provides a suction passageway and a second one of the lumens receives a laser fiber which delivers laser energy through the second lumen and beyond the distal end of the elongated member. The medical device further includes a handle coupled to the proximal end of the elongated member. The handle includes a housing which defines a cavity, a first proximal opening, and a second proximal opening. The first proximal opening receives the laser fiber and allows the laser fiber to pass through the cavity and the second lumen and out of the distal end of the elongated member. The handle further includes a suction tube disposed within the cavity and in fluid communication with the first lumen and the second proximal opening. The suction tube is flexible and selectively collapsible to control suction through the first lumen. The handle further includes a positioning mechanism disposed entirely within the cavity. The positioning mechanism is in contact with the laser fiber and retains the laser fiber in a position within the second lumen while allowing the laser fiber to be moved longitudinally within the second lumen by manual manipulation of a portion of the laser fiber external to the handle by an operator of the medical device.

In one embodiment, the handle further includes a suction control mechanism for controlling a suction path within the suction tube. The suction control mechanism crimps the suction tube and seals the suction path when in a first position and uncrimps the suction tube and opens the suction path when in a second position. The suction control mechanism includes a button or a lever.

In some embodiments, the dual-lumen elongated member includes a transparent material or a translucent material. In other embodiments, the dual-lumen elongated member includes a rigid material or a flexible material.

In some embodiments the medical device further includes a drainage tube external to the housing. The drainage tube includes a proximal end and a distal end. The distal end of the drainage tube is in fluid communication with the second proximal opening and the proximal end of the drainage tube is in fluid communication with a suction pump.

In other embodiments, the distal end of the dual-lumen elongated member includes a tapered end. An outside diameter the first one of the lumens at the tapered end is smaller than an outside diameter of the first one of the lumens at the proximal end.

In still another embodiment, the handle further comprises a fiber clip for holding the laser fiber extending out of the first proximal opening.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3A is an illustrative view of inside the housing of a medical suction device depicting the suction function deactivated according to one embodiment of the invention.

FIG. 3B is an illustrative view of inside the housing of the medical suction device shown in FIG. 3A with the suction function activated.

FIG. 5 is an illustrative cross-sectional top view of a medical suction device depicting a laser fiber positioning mechanism according to one embodiment of the invention.

FIG. 6 is an illustrative cross-sectional top view of a medical suction device depicting a laser fiber positioning mechanism according to another embodiment of the invention.

FIG. 10A is an illustrative diagram of a suction device according to another embodiment of the invention.

FIG. 10B is an illustrative perspective view of a distal end of the suction device shown in FIG. 10A.

DESCRIPTION

The invention relates generally to medical suction devices and more particularly to suction devices that receive and allow the use of an object-destroying or object-fragmenting device such as a laser fiber. The suction device together with the laser fiber (or other destruction/fragmentation mechanism) typically are introduced into the body of a patient through a channel of a scope, such as a rigid, semi-rigid, or flexible nephroscope, to fragment and aspirate objects and fragments of objects, such as stones, other calculi, and/or tissue, as well as fragments thereof.

Figure 1A:
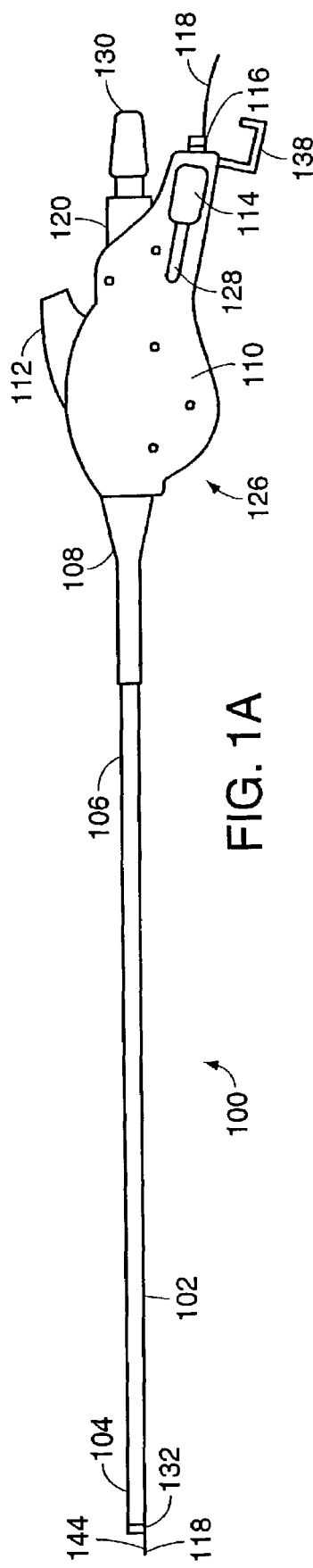
FIG. 1A is an illustrative side view of a medical suction device according to one embodiment of the invention.
Figure 1B:
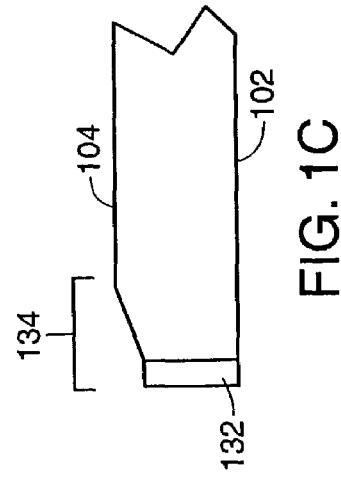
FIG. 1B is an illustrative perspective view of a distal end of the medical suction device shown in FIG. 1A.
Figure 1C:
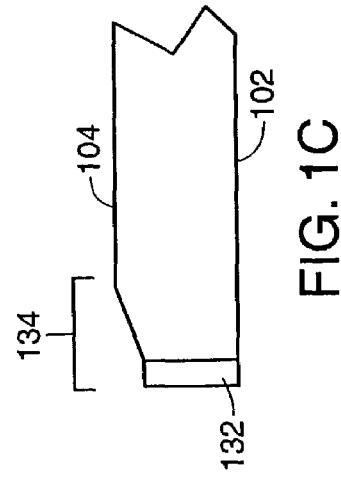
FIG. 1C is an illustrative side view of the distal end of the medical suction device shown in FIG. 1A.
Figure 1D:
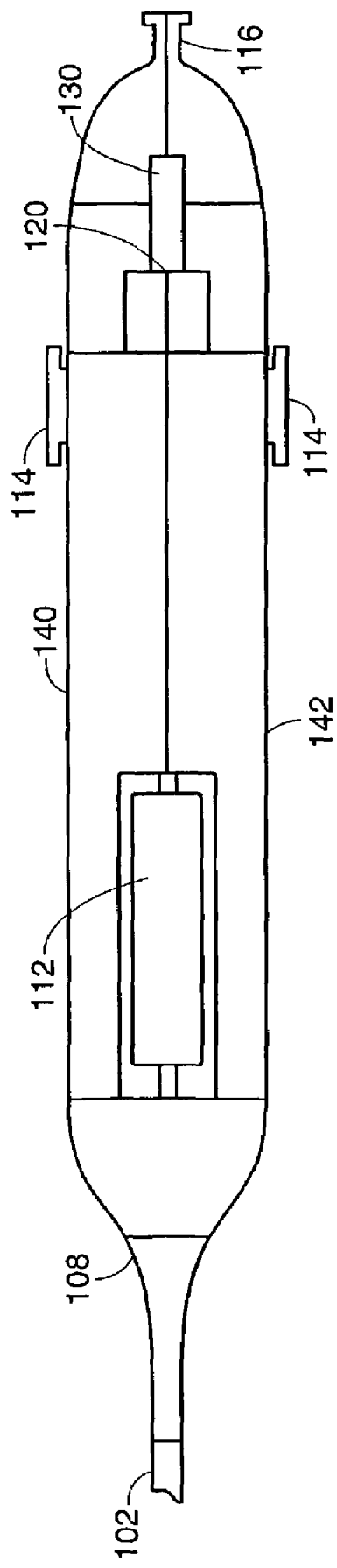
FIG. 1D is an illustrative top view of the medical suction device shown in FIG. 1A.

Referring to FIGS. 1A, 1B, and 1C, in one embodiment, the medical suction device 100 includes a dual-lumen elongated member 102 and a handle 126. The dual-lumen elongated member 102 includes a distal end 104, a proximal end 106, a first lumen 122, and a second lumen 124. The dual-lumen elongated member 102 includes on the distal end 104 a tapered tip 134. The tapered tip can 134 include a bright colored marker 132. In one embodiment, the dual-lumen elongated member 102 is constructed of a clear or translucent material which enables a user to easily identify any blockage in the first lumen 122. In other embodiments, the dual-lumen elongated member 102 can be constructed of polymeric or metallic material and can be rigid, semi-rigid, or flexible. The dual-lumen elongated member 102 is typically produced through an extrusion process.

The handle 126 includes a housing 110, a strain relief 108, a suction actuation button ("suction button") 112, a suction port 120, a suction connector 130, a laser fiber port 116, a slide bar 114, and a fiber clip 138. The housing 110 includes a first housing portion 142 and a second housing portion 140. The suction connector 130 is in communication with the first lumen 122 via a suction tube (discussed in further detail below) and extends out of the suction port 120. In some embodiments, the handle 126 is constructed of a polymeric or metallic material and is typically produced through an injection molding or machining processes. In some embodiment, the housing 110 is constructed of a polymeric, ceramic, or metallic material and is typically produced through a stamping, molding, or machining process.

Figure 2:
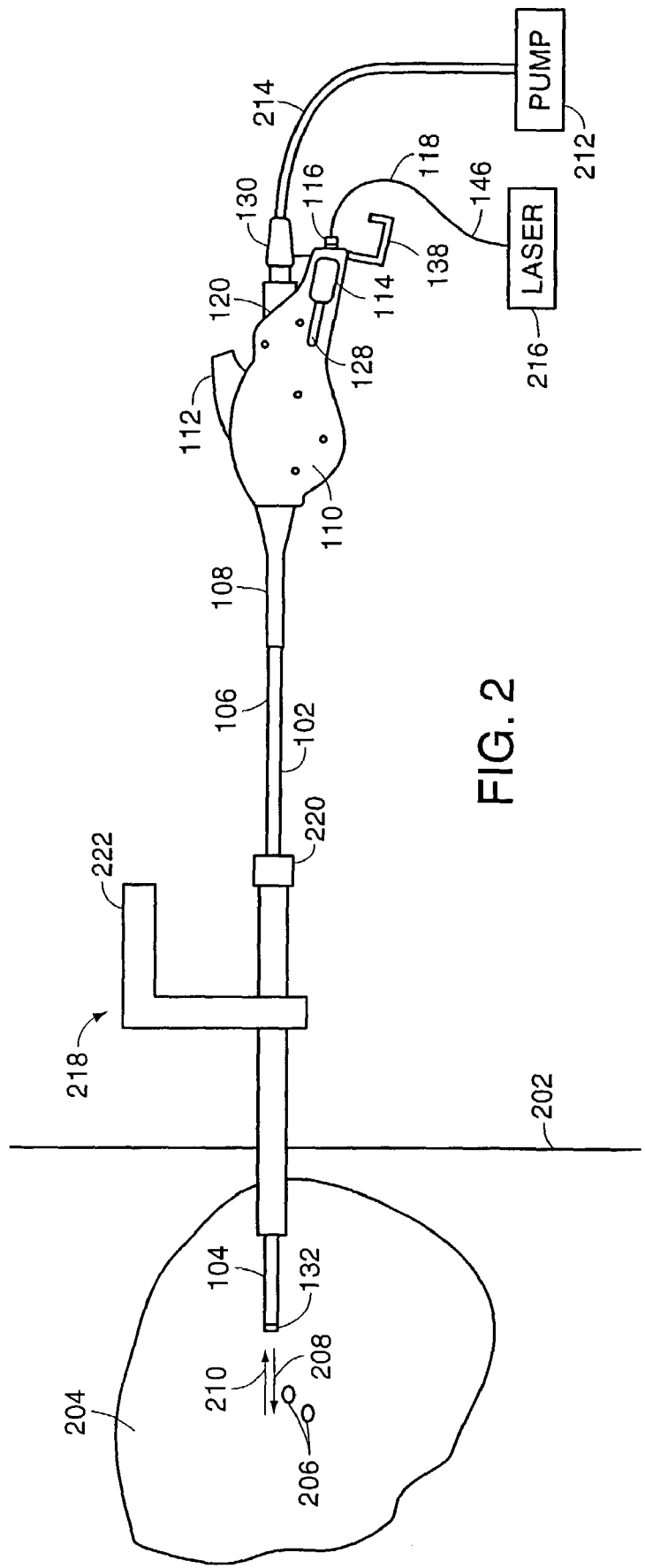
FIG. 2 is an illustrative view of a medical suction device with a distal end disposed in a kidney according to one embodiment of the invention.

Referring to FIGS. 1A and 2, in one illustrative use, an incision is made in a patient 202 and a scope, such as nephroscope 218, for example, is inserted into a patient's organ, such as a kidney 204. The distal end 144 of a laser fiber 118 is inserted into the laser fiber port 116, fed through the housing 110, and into the second lumen 124. The laser fiber 118 is advanced through the second lumen 124 until the distal end 144 of the laser fiber 118 reaches the end of the second lumen 124. The laser fiber 118 is then secured to a portion of the slide bar 114 that is disposed in the housing 110 and discussed in further detail below. The proximal end 146 of the laser fiber 118 is then connected to an energy source, such as a Holmium laser 216, for example. Any excess laser fiber 118 extending between the laser fiber port 116 and the laser 216 can be coiled and secured by the fiber clip 138.

The dual-lumen elongated member 102 is inserted into the nephroscope 218 through port 220 and advanced through the nephroscope 218 until at least the distal end 104 extends out of the nephroscope 218 and into the patient's kidney 204. An external suction tube 214 is connected to a suction pump 212 and the suction connector 130. Suction through the first lumen 122 is controlled by the suction button 112. When the suction button 112 is in a first (default) position, suction through the first lumen 122 is deactivated. When the suction button 112 is pressed, suction through the first lumen 122 is activated.

After a physician, or other medical personnel, inserts the dual-lumen elongated member 102 into the patient's kidney 204 through the nephroscope 218, the physician looks through the nephroscope eyepiece 222 to locate an object for removal, such as a kidney stone 206, and moves the distal end 104 of the dual-lumen elongated member 102 close to the kidney stone 206. The physician can also manually move the laser fiber 118 longitudinally into or out of the second lumen 124 by moving the slide-bar 114 longitudinally. Moving the laser fiber 118 in this manner allows the physician to more accurately position the laser fiber 118 near the kidney stone 206.

After the laser fiber 118 is positioned, the laser 216 is activated. The laser beam (indicated by arrow 208), which can be either a constant beam or an intermittent pulse, strikes the kidney stone 206 and breaks the kidney stone 206 into smaller debris. As (and/or after) the kidney stone 206 breaks up, the physician presses the suction button 112. When the suction button 112 is pressed, suction is activated in the first lumen 122 and the debris in the kidney 204 is aspirated into (as indicated by arrow 210) the first lumen 122. The debris is drawn through the first lumen 122, through the housing 110, and out of the suction connector 130. The debris is further drawn through the external suction tube 214 and ultimately discarded. In one embodiment the first lumen 122 can aspirate an object of up to one and a half millimeters in diameter. After the debris in the kidney 206 is completely removed, the suction button 112 is released and suction through the first lumen 122 is deactivated. This process is repeated until all the kidney stones 206 in the kidney 204 are removed. Alternatively, suction from the first lumen 122 can used to prevent the kidney stone 206 from moving before laser energy is applied. As the kidney stone 206 is fragmented, the debris is drawn into the first lumen 122. A benefit of this method is that the kidney stones 206 are removed more easily and quickly.

Referring again to FIG. 1B, in one embodiment, the distal end 104 of the dual-lumen elongated member 102 includes a tapered tip 134. The opening 136 of the first lumen 122 at the tapered tip 134 has a smaller diameter than the diameter of the rest of the first lumen 122. The tapered tip 134 minimizes clogging of the first lumen 122 by only allowing in debris that is smaller than the diameter of the first lumen 122. In one embodiment, the length of the tapered tip 134 is five millimeters. In another embodiment, the tapered tip 134 includes a bright color marker 132. The bright color marker 132 allows the physician to easily locate the distal end 104 of dual-lumen elongated member 102 when the distal end 104 is disposed within a patient and being viewed through a nephroscope. Additionally, the bright color marker 132 allows the physician to be able to distinguish the first (suction) lumen 122 from the laser beam emanating from the second lumen 124. The bright color marker 132 can also be used as an ultrasonic or fluoroscopic marker for locating the distal end 104 within the patient's body.

In some embodiments, the tapered tip 134 is produced by heat forming or heat bonding polymeric or metallic material to the distal end 104 of the dual-lumen elongated member 102. In other embodiments, the bright color marker 132 is a molded component coupled to the tapered tip 134. In still other embodiments, the bright color marker 132 is painted on the tapered tip 134, or produced by a chemical process.

Referring to FIGS. 3A and 3B, in one embodiment, a suction tube 302 disposed within the housing 110 connects the dual-lumen elongated member 102 to the suction connector 130. The suction connector 130 is positioned such that the portion of the suction connector 130 that connects to the suction tube 302 is disposed within the housing 110 with the rest of the suction connector 130 extending through the suction port 120. When the suction button 112 is not pressed (default position), the suction button 112 is positioned such that a rigid member 304 presses against the suction tube 302 thereby crimping the suction tube 302 and preventing suction from the pump 212 (FIG. 2) from extending through the first lumen 122. This feature allows the physician to manipulate the medical suction device 100 within the patient's body without removing excessive amounts of body fluids.

When the suction button 112 is pressed, the suction button 112 is positioned such that the rigid member 304 no longer presses against the suction tube 302 resulting in suction extending through the first lumen 122. As long as the suction button 112 is pressed, suction through the first lumen 122 is active. As soon as the suction button 112 is released, suction through the first lumen 122 is deactivated. In another embodiment, a lever is used to selectively enable and disable suction in the same way the suction button 112 is used to selectively enable and disable suction. In another embodiment, the suction through the first lumen 122 can be reversed and used for irrigation by connecting the suction connector 120 to a pump that provides bi-directional flow.

In some embodiments, the suction tube 302 is constructed of an elastomeric material with a memory. In other embodiments, the suction connector 120 is constructed of a polymeric material with a smooth bore and is typically produced through an injection molding or machining process.

In another embodiment, before the medical suction device 100 is first used, a shipping tab (not shown) is first removed from the handle 126. The shipping tab is positioned proximate to the suction button 112 and holds the suction button 112 in the pressed position thereby keeping the suction tube 302 uncrimped. After the shipping tab is removed, the suction button 112 functions as previously described.

Figure 4:
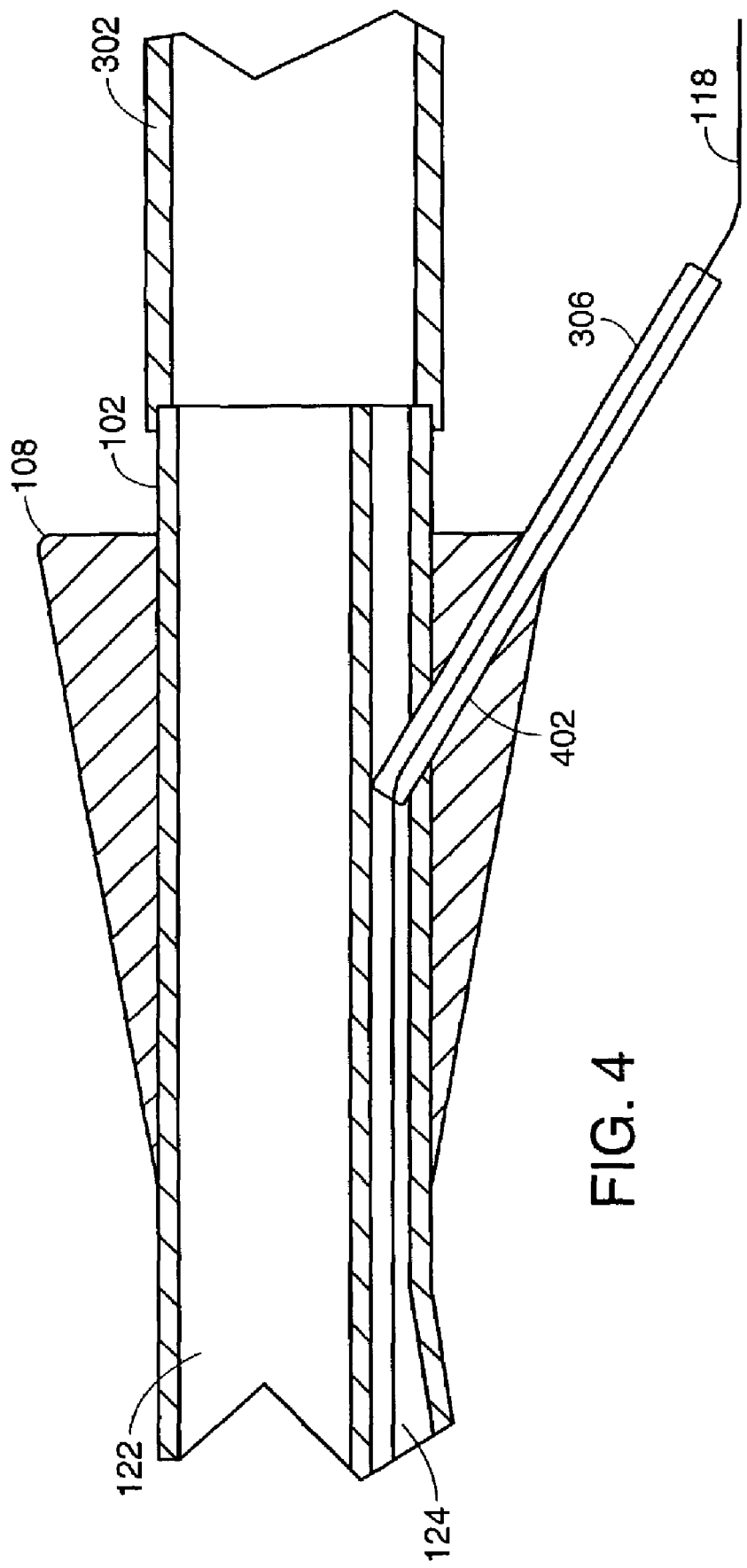
FIG. 4 is an illustrative cross-sectional side view of a dual-lumen elongated member according to one embodiment of the invention.

Referring to FIGS. 3A, 3B, and 4, in one embodiment, an access hole 402 is cut into a wall of the dual-lumen elongated member 102 to provide an separate access point to the second lumen 124. An extension tube 306 is inserted into the access hole 402 and is held in place by glue or friction. The intersection of the dual-lumen elongated member 102 and the extension tube 306 is held together and reinforced by strain relief 108. The strain relief 108 also prevents the dual-lumen elongated member 102 from kinking when inserted into a scope and acts as a plug to prevent body fluids from flowing back through the scope. The extension tube 306 provides a path for the laser fiber 118 to enter the second lumen 124 from within the housing 110 because the end of the dual-lumen elongated member 102 is coupled to the suction tube 302. The extension tube 306 also blocks the suction from the suction tube 302 and provides support for the laser fiber 118.

In some embodiments, the access hole 402 can be created by a hole punch, a hot stamp, a scalpel, or a drill press. The extension tube 306 is constructed of polymeric or metallic material and is typically produced through an extrusion or dipping process. The strain relief 108 is constructed of polymeric or metallic material and is typically produced through a machining or molding process.

Referring to FIGS. 1A, 1B, 4, and 5, in one embodiment, the distal end 144 of the laser fiber 118 is inserted into laser fiber port 116 and fed through the housing 110 and into the extension tube 306. The laser fiber 118 is then fed through the extension tube 306 and into the second lumen 124. The laser fiber 118 is fed through the second lumen 124 until the distal end of the laser fiber 118 reaches the tapered tip 134. However, prior to entering the extension tube 306, the laser fiber 118 is fed through a clamp 504 which is part of a laser fiber positioning system 502 that is disposed within the housing 110 and coupled to at least one slide-bar 114 through an opening 128. As the laser fiber 118 is fed though the various parts of the medical suction device 100, the clamp 504 is held in an unclamped state thereby allowing the laser fiber 118 to move through the clamp 504. Once the distal end 144 of the laser fiber 118 reaches the tapered tip 134, the clamp 504 clamps the laser fiber 118. Thereafter, the laser fiber 118 is manually advanced and retracted by longitudinally sliding the slide bar 114 as shown by arrow 506.

In some embodiments, the clamp 504 is constructed of a polymeric, ceramic, or metallic material and is typically produced through a molding or machining process. Additionally, the clamp 504 includes elastomeric pads or covers which cushion and prevent damage to the laser fiber 118 when clamped. In other embodiments, the slide bar 114 is constructed of a polymeric or metallic material and is typically produced through an injection molding or machining process.

Referring to FIG. 6, in another embodiment, the laser fiber 118 is positioned between two thumbwheels 602 and fed through a grommet 604. The laser fiber 118 is held in position by the grommet 604 through friction and can be retracted or advanced along the second lumen 124 when the thumbwheels 602 are manually rotated clockwise and counterclockwise. In another embodiment, the thumbwheels 602 are not in constant contact with the laser fiber 118. In this embodiment, the thumbwheels 602 must be squeezed or pressed inward toward the housing 110 to first make contact with the laser fiber 118 and held in the squeezed positioned while being rotated in order to advance and retract the laser fiber 118.

Figure 7:
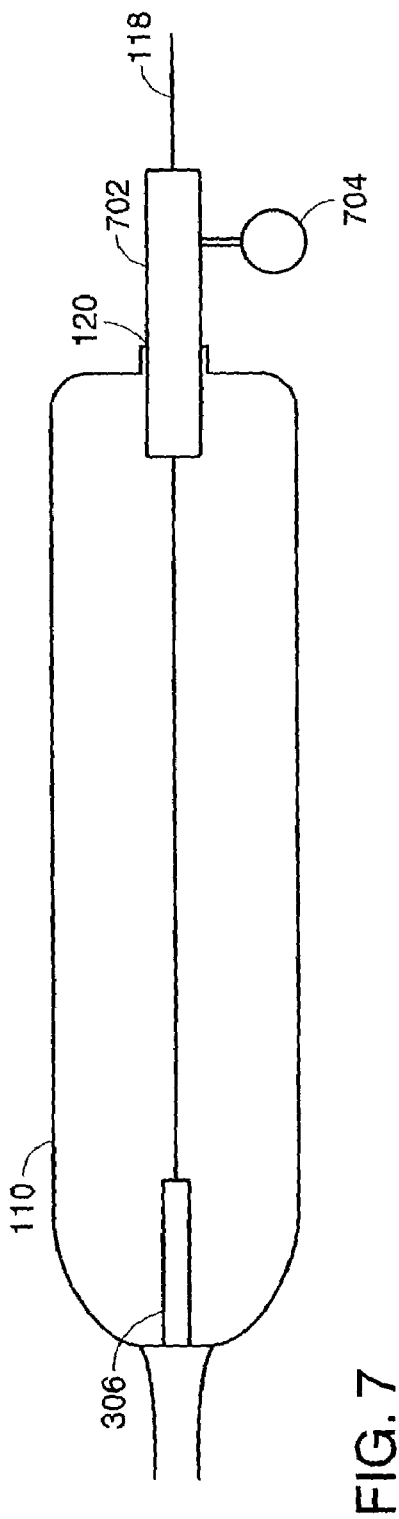
FIG. 7 is an illustrative cross-sectional top view of a medical suction device depicting a laser fiber positioning mechanism according to still another embodiment of the invention.

Referring to FIG. 7, in still another embodiment, the laser fiber 118 is fed through and gripped by a plunger 702 that moves in and out of laser fiber port 120. In this embodiment, the laser fiber 118 is selectively retracted and advanced by sliding the plunger 702 in and out of the laser fiber port 120 using a thumb-ring 704. When the plunger 702 is not manually moved, the plunger 702 held motionless through a friction connection with laser fiber port 120.

Figure 8:
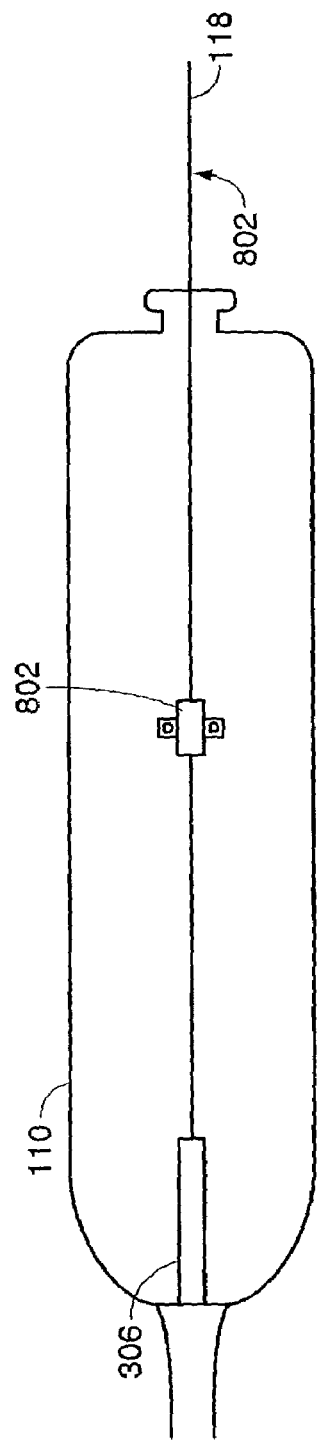
FIG. 8 is an illustrative cross-sectional top view of a medical suction device depicting a laser fiber positioning mechanism according to yet another embodiment of the invention.

Referring to FIG. 8, in yet another embodiment, the laser fiber 118 is fed through a grommet 802 and held in position by friction. In this embodiment, the laser fiber 118 is selectively retracted and advanced by gripping the laser fiber 118 between two fingers at, or near, location 802 and pulling the laser fiber 118 out of the housing 110 or pushing the laser fiber 118 into the housing. The selected position of the laser fiber 118 is maintained by the friction from the grommet 802. In yet another embodiment, the selected position of the laser fiber 118 is maintained by the combined friction from the second lumen 124, the extension tube 306, and the laser fiber connector port 116.

Figure 9:
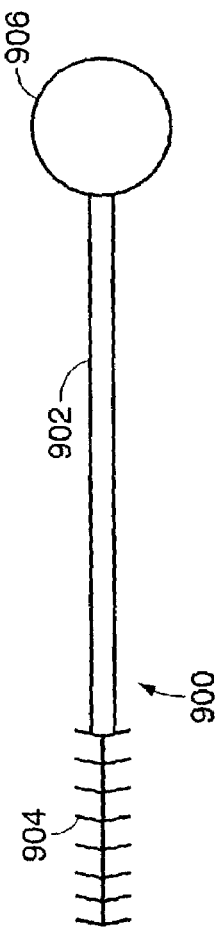
FIG. 9 is an illustrative diagram of a device used to clean a medical suction device according to one embodiment of the invention.

Referring to FIG. 9, in some embodiments, a cleaning device 900 is included with the dual-lumen access device 100. The cleaning device includes handle 906, shaft 902, and bristles 904. The cleaning device is used to remove debris trapped in the first lumen 122 by inserting the cleaning-device 900 into the distal end 104 of the first lumen 122 and manually moving the cleaning device 900 longitudinally in the first lumen.

Referring to FIGS. 10A and 10B, in an alternative embodiment, the medical suction device 1000 includes a single-lumen elongated member 1002 and a handle 1004. The single-lumen elongated member 1002 includes a distal end 1010, a proximal end 1020, and a lumen 1012. The handle 1004 includes a suction actuation button 1006, a suction tube 1008, and a laser fiber port 1018. The single-lumen elongated member 1002 further includes a laser fiber retention clip 1016. The housing 110 includes a first housing portion 142 and a second housing portion 140. The suction tube 1008 is in communication with the lumen 1012 through a tube (not shown) disposed in the handle. A laser fiber 1014 is fed through the laser fiber port 1018, fed through the handle, and through the lumen 1012 until the laser fiber 1014 reaches the distal end 1010 of the single-lumen elongated member 1002. The laser fiber 1014 is restrained at the distal end 1010 with the laser fiber retention clip 1016.

Variations, modifications, and other implementations of what is described herein may occur to those of ordinary skill without departing from the spirit and scope of the invention. Accordingly, the invention is not to be limited only by the preceding illustrative description.

What is claimed is:

1. A medical device, comprising:
    an elongated member having a proximal end, a distal end, a first lumen extending longitudinally through the elongated member, and a second lumen, separate from the first lumen, extending longitudinally through the elongated member, each of the first and second lumens terminating at separate apertures at the distal end of the elongated member, the first lumen for providing a suction passageway, the second lumen for receiving a laser fiber for delivering laser energy through the second lumen and beyond the distal end of the elongated member;
    a suction tube disposed within a handle and in fluid communication with the first lumen, the suction tube being flexible and selectively collapsible to control suction through the first lumen;
    a laser fiber positioning mechanism having at least a portion thereof disposed within the handle for controlling longitudinal movement of the laser fiber within the second lumen; and
    wherein a distal end portion of the elongated member is tapered such that a cross-sectional area of the first lumen along the tapered portion of the elongated member is less than that of a remaining portion of the first lumen.

2. The medical device of claim 1, wherein the first lumen has a semicircular cross-sectional shape.

3. The medical device of claim 2, wherein the second lumen has a circular cross-sectional shape.

4. The medical device of claim 1, wherein the second lumen has a constant cross-sectional shape along the length thereof.

5. The medical device of claim 1, wherein the distal tapered portion comprises a translucent material.

6. The medical device of claim 1, wherein the distal tapered portion exhibits a color different from that of the remaining portion of the elongated member.

7. The medical device of claim 2, wherein an arc of the semicircular cross-sectional shape of the first lumen is contiguous with an external surface of the elongated member.

8. The medical device of claim 3, wherein a circumference of the circular cross-sectional shape of the second lumen is not contiguous with an external surface of the elongated member.

9. The medical device of claim 1, wherein the laser fiber positioning mechanism comprises a clamp disposed within the housing, the laser fiber longitudinally movable through the clamp.

10. The medical device of claim 9, wherein the clamp comprises elastomeric pads for cushioning the laser fiber when restrained therein.

11. The medical device of claim 9, wherein the clamp restrains the laser fiber when a distal end of the laser fiber reaches the distal end of the elongated member.

12. The medical device of claim 1, wherein the laser fiber positioning mechanism comprises a grommet disposed within the housing.

13. The medical device of claim 12, wherein the laser fiber positioning mechanism further comprises a pair of rotatable thumbwheels having at least a portion thereof disposed externally to the housing, the thumbwheels controlling longitudinal movement of the laser fiber within the second lumen through the grommet.

14. The medical device of claim 13, wherein the thumbwheels contact the laser fiber when pressed toward the housing.

15. The medical device of claim 1, wherein the laser fiber positioning mechanism further comprises a plunger having at least a portion thereof disposed externally to the housing, the plunger controlling longitudinal movement of the laser fiber within the second lumen.

16. The medical device of claim 15, wherein the laser fiber positioning mechanism further comprises a thumb-ring attached to the external portion of the plunger.

17. A medical device, comprising:
a dual-lumen elongated member comprising a proximal end, a distal end, a first lumen, and a second lumen, the first lumen for providing a suction passageway, the second lumen for receiving a laser fiber for delivering laser energy through the second lumen and beyond the distal end of the elongated member;
a suction tube disposed within a cavity of a handle and in fluid communication with the first lumen, the suction tube being flexible and selectively collapsible to control suction through the first lumen; and
a laser fiber positioning mechanism comprising:
a clamp disposed within the handle for restraining the laser fiber, at least one slide-bar disposed external to the handle and coupled to the clamp such that longitudinal movement of the slide bar results in longitudinal movement of the laser fiber within the second lumen.

18. The medical device of claim 17, wherein a portion of the elongated member comprises a clear material.

19. The medical device of claim 17, wherein the distal end of the elongated member includes a colored marker.

20. The medical device of claim 17, wherein a distal end of the first lumen has a smaller diameter than a diameter of a remaining portion of the first lumen.

21. The medical device of claim 17, further comprising a pump configured for selective connection with the second proximal opening to provide irrigation through the first lumen.

22. The medical device of claim 1, wherein the positioning mechanism comprises rotatable thumbwheels for controlling longitudinal movement of the laser fiber.

23. The medical device of claim 1, wherein the positioning mechanism comprises a plunger for controlling longitudinal movement of the laser fiber within the lumen.

24. The medical device of claim 1, wherein the suction tube includes no openings between a distal end and a proximal end of the suction tube.

25. The medical device of claim 1, wherein the handle is configured to crimp the suction tube to control suction.

26. A medical device, comprising:
a dual-lumen elongated member comprising a proximal end, a distal end, a first lumen having a semicircular cross-sectional shape, and a second lumen having a circular cross-sectional shape, the first lumen for providing a suction passageway, the second lumen for receiving a laser fiber for delivering laser energy through the second lumen and beyond the distal end of the elongated member;
a suction tube disposed within a cavity of a handle and in fluid communication with the first lumen, the suction tube being flexible and selectively collapsible to control suction through the first lumen; and
a laser fiber positioning mechanism having at least a portion thereof disposed within the handle for controlling longitudinal movement of the laser fiber within the second lumen.

27. The medical device of claim 26, wherein an arc of the semicircular cross-sectional shape of the first lumen is contiguous with an external surface of the elongated member.

28. The medical device of claim 26, wherein a circumference of the circular cross-sectional shape of the second lumen is not contiguous with an external surface of the elongated member.

29. The medical device of claim 28, wherein the first lumen has a greater cross-sectional area than the second lumen.

30. A medical device, comprising:
an elongated member having a proximal end, a distal end, a first lumen extending longitudinally through the elongated member, and a second lumen, separate from the first lumen, extending longitudinally through the elongated member, each of the first and second lumens terminating at separate apertures at the distal end of the elongated member at the same longitudinal location, the first lumen for providing a suction passageway, the second lumen for receiving a laser fiber for delivering laser energy through the second lumen and beyond the distal end of the elongated member;
a suction tube disposed within a handle and in fluid communication with the first lumen, the suction tube being flexible and selectively collapsible to control suction through the first lumen;
a laser fiber positioning mechanism having at least a portion thereof disposed within the handle for controlling longitudinal movement of the laser fiber within the second lumen; and
wherein the first lumen has a greater cross-sectional area than the second lumen.

31. The medical device of claim 30, wherein the first lumen has a semicircular cross-sectional shape.

32. The medical device of claim 31, wherein the second lumen has a circular cross-sectional shape.

33. A medical device, comprising:
an elongated member having a proximal end, a distal end, a first lumen extending longitudinally through the elongated member, and a second lumen, separate from the first lumen, extending longitudinally through the elongated member, the first lumen for providing a suction passageway, the second lumen for receiving a laser fiber for delivering laser energy through the second lumen and beyond the distal end of the elongated member;
a suction tube disposed within a handle and in fluid communication with the first lumen, the suction tube being flexible and selectively collapsible to control suction through the first lumen;
a laser fiber positioning mechanism having at least a portion thereof disposed within the handle for controlling longitudinal movement of the laser fiber within the second lumen;
wherein a distal end portion of the elongated member is tapered; and
wherein the first lumen has a greater cross-sectional area than the second lumen.

34. The medical device of claim 33, wherein the first lumen has a semicircular cross-sectional shape.

35. The medical device of claim 34, wherein the second lumen has a circular cross-sectional shape.

36. The medical device of claim 26, wherein the suction tube includes no openings between a distal end and a proximal end of the suction tube.

37. The medical device of claim 26, wherein the handle is configured to crimp the suction tube to control suction.

38. The medical device of claim 30, wherein the suction tube includes no openings between a distal end and a proximal end of the suction tube.

39. The medical device of claim 30, wherein the handle is configured to crimp the suction tube to control suction.

40. The medical device of claim 33, wherein the suction tube includes no openings between a distal end and a proximal end of the suction tube.

41. The medical device of claim 33, wherein the handle is configured to crimp the suction tube to control suction.

42. A medical device, comprising:
- an elongated member having a proximal end, a distal end, a first lumen extending longitudinally through the elongated member, and a second lumen, separate from the first lumen, extending longitudinally through the elongated member, each of the first and second lumens terminating at separate apertures at the distal end of the elongated member, the first lumen for providing a suction passageway, the second lumen for receiving a laser fiber for delivering laser energy through the second lumen and beyond the distal end of the elongated member;
- a suction tube disposed within a handle and in fluid communication with the first lumen, the suction tube being flexible and selectively collapsible to control suction through the first lumen; and
- a laser fiber positioning mechanism including a clamp disposed within the handle for restraining the laser fiber and at least one slide-bar disposed external to the handle and coupled to the clamp such that longitudinal movement of the slide bar results in longitudinal movement of the laser fiber beyond the aperture of the second lumen.

43. The medical device of claim 42, wherein the suction tube includes no openings between a distal end and a proximal end of the suction tube.

44. The medical device of claim 42, wherein the handle is configured to crimp the suction tube to control suction.

45. The medical device of claim 17, wherein the distal end of the elongated member has a tapered tip, and the first lumen is defined at its distal end by the tapered tip.

46. The medical device of claim 17, wherein the suction tube includes no openings between a distal end and a proximal end of the suction tube.

47. The medical device of claim 17, wherein the handle is configured to crimp the suction tube to control suction.

\* \* \* \* \*